United States Patent

Ishikawa et al.

[11] 4,136,188
[45] Jan. 23, 1979

[54] TREATMENT OF DIABETES WITH 2-SUBSTITUTED-1,3-DIAZACYCLIC COMPOUNDS

[75] Inventors: Fumiyoshi Ishikawa, Funabashi; Akira Kosasayama, Yotsukaidomachi; Yoshifumi Watanabe, Funabashi; Yasushi Abiko, Matsudo; Kin-Ya Kameda, Narashino; Shin-etu Ono, Chiba, all of Japan

[73] Assignee: Daiichi Seiyaku Co., Ltd., Tokyo, Japan

[21] Appl. No.: 699,761

[22] Filed: Jun. 25, 1976

[51] Int. Cl.² ............................................. A61K 31/415
[52] U.S. Cl. .......................... 424/273 R; 260/239 BC; 260/244.4; 424/241; 424/251; 424/263; 424/266; 544/242; 544/330; 544/331; 544/333; 544/335; 546/278
[58] Field of Search ........................ 260/309.6, 296 R; 424/273, 263; 548/355

[56] References Cited

U.S. PATENT DOCUMENTS

| | | | |
|---|---|---|---|
| 2,604,473 | 7/1952 | Sperber et al. | 260/293.68 |
| 2,676,964 | 4/1954 | Sperber et al. | 260/309.6 |
| 2,899,441 | 8/1959 | Dornfeld | 260/309.6 |
| 3,359,274 | 12/1967 | Warner | 260/309.6 |
| 3,840,524 | 10/1974 | Grisar et al. | 260/296 R |

FOREIGN PATENT DOCUMENTS 283583  10/1952  Switzerland ............................ 260/309.6

OTHER PUBLICATIONS

Faust et al., J. Org. Chem., 1961, vol. 26, pp. 4044–4047.
Harsanyi et al., Chem. Abst., 1964, vol. 61, col. 5660.
Jilek et al., J. Chem. Soc. (London), 1950, pp. 188–190.
Pirvu Chem. Abst., 1971, vol. 75, No. 118270q.
Walter Chem. Abst. 1970, vol. 72, No. 31790y.

*Primary Examiner*—Natalie Trousof
*Attorney, Agent, or Firm*—Sughrue, Rothwell, Mion, Zinn and Macpeak

[57] ABSTRACT

2-substituted-1,3-diazacyclic compounds of the formula:

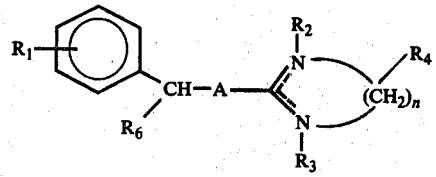

wherein $R_1$ represents a hydrogen atom, a halogen atom, a lower alkyl group or a lower alkoxy group; $R_2$ represents a hydrogen atom, a lower alkoxycarbonyl group, an aliphatic acyl group or an aromatic acyl group, the aromatic ring of which may have one or more substituents selected from a halogen atom, a lower alkyl group, a lower alkoxy group, an acyl group and an acyloxy group; $R_3$ represents a hydrogen atom, a lower alkyl group, a lower hydroxyalkyl group or an aralkyl group; $R_4$ represents a hydrogen atom, a lower alkyl group or an aryl group; $R_6$ represents a cyclohexyl group, a pyridyl group or a phenyl group which may have a substituent selected from a halogen atom, a lower alkyl group and a lower alkoxy group; A represents -N=, an -N(lower alkyl)- group or a methylene group; n represents an integer of from 2 to 4, and a dotted line indicates that a double bond is optional; salts of such derivatives; and the method for preparing such compounds and their salts; the compounds and their salts having a distinct anti-diabetic activity in humans and animals.

3 Claims, No Drawings

TREATMENT OF DIABETES WITH 2-SUBSTITUTED-1,3-DIAZACYCLIC COMPOUNDS

BACKGROUND OF THE INVENTION

1. Field of the Invention

This invention relates to 2-substituted-1,3-diazacylic compounds and to processes for preparing the same.

2. Description of the Prior Art

A representative anti-diabetic compound structurally similar to those of this invention, Benzhydryl Lactamimide as shown in the following chemical formula

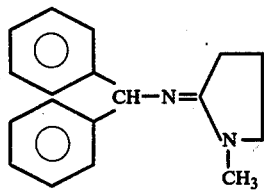

(Q)

is known. Such is described in Journal of Medical Chemistry, Vol 16 p 885-892 (1973).

Such compound [hereinafter defined as Compound (Q)], however, has not proved satisfactory for clinical use because of its undesirable side effects or insufficient activities, as shown hereinafter.

SUMMARY OF THE INVENTION

It is an object of this invention to provide compounds which have excellent hypoglycemic and Blood Platelet Aggregation Inhibitory activities and can be safely used clinically without deleterious side effects.

Another object is to provide methods for manufacturing such compounds and their salts. More particularly, this invention provides novel 2-substituted-1,3-diazacyclic compounds represented by general formula (1)

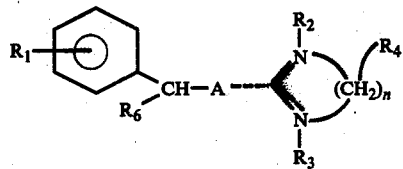

(1)

wherein $R_1$ represents a hydrogen atom, a halogen atom, a lower alkyl group or a lower alkoxy group; $R_2$ represents a hydrogen atom, a lower alkoxycarbonyl group, an aliphatic acyl group or an aromatic acyl group, the aromatic ring of which may have one or more substituents selected from a halogen atom, a lower alkyl group, a lower alkoxy group, an acyl group and an acyloxy group; $R_3$ represents a hydrogen atom, a lower alkyl group, a lower hydroxyalkyl group or an aralkyl group; $R_4$ represents a hydrogen atom, a lower alkyl group or an aryl group; $R_6$ represents a cyclohexyl group, a pyridyl group or a phenyl group which may have a substituent selected from a halogen atom, a lower alkyl group and a lower alkoxy group; A represents $-N=$, an -N(lower alkyl)- group or a methylene group; n represents an integer of from 2 to 4, and a dotted line indicates that a double bond is optional with the proviso that when A is an -N(lower alkyl)- group or a -$CH_2$- group, $R_2$ and $R_3$ cannot simultaneously be present. $R_2$ and $R_3$ can both be present simultaneously when A represents $-N=$.

This invention also relates to salts of such compounds and to methods of preparing such compounds and their salts.

The compounds have a distinct anti-diabetic activity in human beings and animals. Further objects will appear hereinafter.

DETAILED DESCRIPTION OF THE INVENTION

The compounds of this invention can be prepared by any of the methods represented by the following reaction schematics (A) to (D).

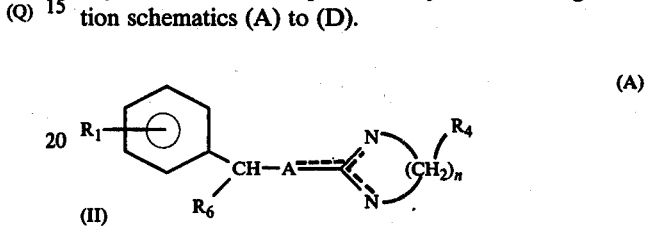

(A)

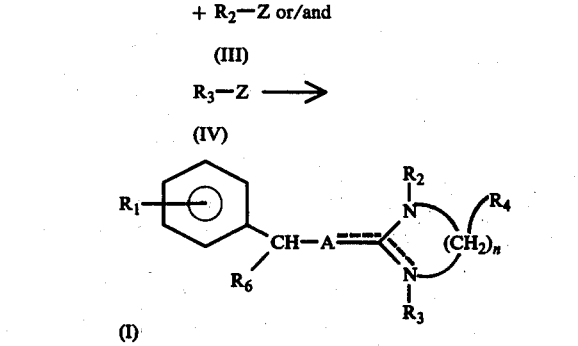

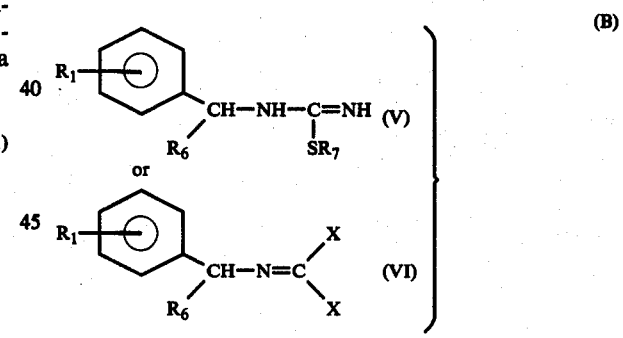

(B)

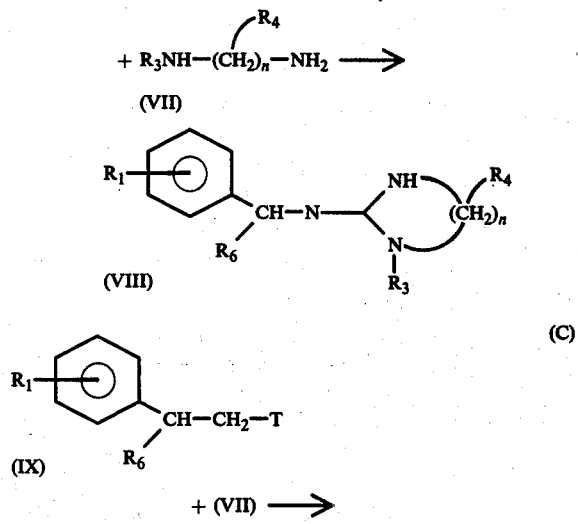

(C)

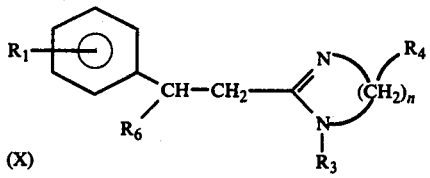
(X)

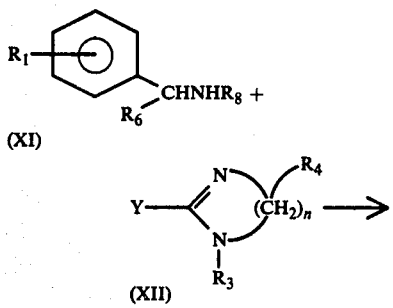
(XI)
(XII)

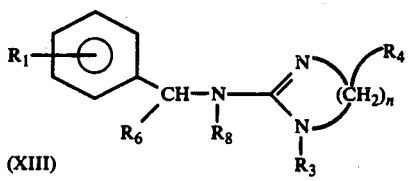
(XIII)

In the above reaction schematics (A) to (D), the generic symbols which are employed have the following meaning:

X represents a halogen atom;
Y represents a halogen atom, an alkylthio group or a nitroamino group;
Z represents a halogen atom, an alkylsulfate group or an acyloxy group;
T represents an amidino group, an iminoether group or a nitrile group;
$R_7$ represents a hydrogen atom or a lower alkyl group;
$R_8$ represents a hydrogen atom or a lower alkyl group; and $R_1$, $R_2$, $R_3$, $R_4$, $R_6$ and n mean the same as defined hereinbefore.

Hereinafter each of the method will be explained more precisely.

Method (A)

The desired compounds in accordance with this invention are produced by reacting raw material (II) with raw materials (III) and/or (IV).

In this synthesis route, alkylation is preferably be conducted prior to acylation. The alkylation is conducted in a suitable solvent at from about room temperature (e.g. 20°–30° C.) up to about the boiling point of the solvent, preferably in the presence of a base, such as an alkali hydride or alkoxide.

The acylation is conducted in a suitable solvent at from about 0° C. up to about 100° C. As a solvent, use is made of an inert solvent, such as diethyl ether, chloroform, benzene pyridine or dimethylformamide. Further, if desired, use can be made of a base such as an amine (e.g. triethylamine), an alkali hydride (e.g. sodium hydride) or an alkali carbonate.

Method (B)

The desired compounds in accordance with this invention can also be produced by reacting as raw materials an isothiuronium compound (V) with a diamine (VII) without a solvent, or in a suitable solvent such as methanol, tetramethylenediamine, etc., at from about 0° C. up to about 200° C.

In place of the isothiuronium compound (V), an isocyanide dihalide (VI) may be reacted with a diamine (VII) at the same conditions.

Method (C)

Some of the compounds of this invention can be produced by reacting raw material (IX) with a diamine (VII) in a suitable solvent, such as toluene or xylene, at the boiling point of the system. More preferably, this reaction is conducted by heating the raw materials without any solvent at from about 100° C. up to about 220° C.

Method (D)

Some of the compounds of this invention can also be produced by reacting raw material (XI) with raw material (XII) in a suitable solvent at from about room temperature up to about 50° C. for several or several tens hours.

As preferred solvents, use is made of an inert solvent such as chloroform, diethyl ether, dioxane or benzene.

The thus obtained compounds of this invention, if desired, can be converted into a pharmaceutically acceptable acid addition salt, such as a hydrochloric acid salt, a hydrobromic acid salt, a sulfuric acid salt, a phosphoric acid salt, a nitric acid salt, an acetic acid salt, an oxalic acid salt, a malonic acid salt, a maleic acid salt, a fumaric acid salt or a methanesulfonic acid salt.

As is apparent from the above description, various methods of preparation can suitably be employed, depending on the kind of 2-substituted-1,3-diazacyclic compound desired.

The compounds of the present invention have a characteristic anti-diabetic activity ordinarily not obtained from known typical agents, such as, tolubutamide.

To demonstrate the superiority of the present compounds, the pharmacological properties of several representative compounds of this invention were compared with those of tolubutamide, phenformin or known compound (Q).

1. Hypoglycemic Activity

1) Dose-effect relationship in normal rats

Five male Wistar rats weighing about 170g were used at each dosage level. An aqueous solution or suspension of the test compound was orally administered at a dose of 25 mg/kg body weight by means of a stomach tube to a rat which had not been fed for 24 hours before administration. 2, 3 and 5 hours after administration, a blood sample was taken from the tail vein of the rat and assayed for glucose by the glucose oxidase method. The results obtained are shown in Table 1.

Table 1

| | Test Compound | | | Decrease in blood glucose (% based on the control) | | |
|---|---|---|---|---|---|---|
| | | $R_2$ | $R_3$ | 2 hrs | 3 hrs | 5 hrs |
| 1 | (benzhydryl-CHN=imidazoline with $R_2$, $R_3$) | —H | —$CH_3$ | 45 | 44 | 40 |
| 2 | | —H | —$CH_2CH_2OH$ | 9 | 31 | 54 |
| 3 | | —$COCH_3$ | —$CH_3$ | 37 | 39 | 39 |
| 4 | | —CO—(phenyl) | —$CH_3$ | 32 | 32 | 19 |
| 5 | | —CO—(furyl) | —$CH_3$ | 29 | 36 | 36 |
| 6 | | —CO—(thienyl) | —$CH_3$ | 36 | 49 | 30 |
| 7 | | —CO—(pyridyl) | —$CH_3$ | 55 | 52 | 39 |
| 8 | (benzhydryl-CHN(CH3)—imidazoline-NH) | — | — | 34 | 42 | 42 |
| 9 | (diphenyl-CHCH2—imidazoline with $R_3$) | — | —H | 32 | 32 | 24 |
| 10 | | — | —$CH_3$ | 49 | 47 | 41 |
| 11 | Tolubutamide | | | 20 | 24 | 20 |
| 12 | Phenformin* | | | 10 | 15 | 15 |
| 13 | (benzhydryl-CHN=pyrrolidine-N-CH3) | | | 34 | 38 | 13 |

*Dose = 100 mg/kg

2) Glucose tolerance test in normal rats

Five male Wistar rats weighing about 200g were used at each dose level. An aqueous solution or suspension of a test compound was orally administered by means of a stomach tube to each rat which had not been fed for 24 hours before administration. One hour after administration, each rat received an intraperitoneal injection of a glucose solution (1 g glucose/kg body weight). Blood samples were taken from the tail vein just before and 15, 30, 60 and 90 minutes after glucose loading, and were assayed for blood glucose. The glucose tolerance of the rats was estimated by the increase in blood glucose during the 90 minutes after glucose loading $$[\sum_{0-90} \Delta BG \text{ (mg/dl)}].$$

The results obtained are shown in Table 2.

Table 2

| | Dose (mg/kg) | $\sum_{0-90} \Delta BG$(mg/dl) | | Increase in glucose tolerance |
|---|---|---|---|---|
| | | Test compound | Control | |
| Tolubutamide | 20* | 83 ± 14 | 121 ± 14 | 31.4% |
| Compound A | 10 | 58 ± 4 | 121 ± 14 | 52.1 |
| Compound B | 10 | 4 ± 12 | 127 ± 8 | 96.9 |
| Compound C | 10 | 94 ± 8 | 127 ± 8 | 26.0 |

*Given 30 minutes prior to glucose loading.

**$[1 - \frac{\sum \Delta BG \text{ (test)}}{\sum \Delta BG \text{ (control)}}] \times 100$.

Compounds A to F in Tables 2 to 8 are some representative compounds of this invention; details are as follows.

Compound A = 1-methyl-2-benzhydryliminoimidazolidine.

Compound B = 2-(2,2-diphenylethyl)-2-imidazoline

Compound C = 1-methyl-2-(2,2-diphenylethyl)-2-imidazoline.

Compound D = 1-methyl-2-benzhydrylimino-3-benzoylimidazolidine.

Compound E = 1-methyl-2-benzhydrylimino-3-thienoylimidazolidine.

Compound F = 1-methyl-2-benzhydrylimino-3-nicotinoyl-imidazolidine.

3) Glucose tolerance test in streptozotocin-induced mildly diabetic rats

An aqueous solution or suspension of a test compound was orally administered to male Wistar rats which had not been fed for 24 hours prior to oral administration and which had been rendered diabetic for about 2 months by a single intravenous injection of streptozotocin (20 mg/kg body weight). Control diabetic rats received water. Unfed (fasted) and fed blood glucose levels of the rats were 89 ± 1∼103 ± 4 mg/dl and 123 ± 2∼189 ± 11 mg/dl, respectively. One hour after administration of the test compound, each rat received an intraperitoneal injection of a glucose solution (1 g glucose/kg body weight). Blood samples were taken from the tail vein just before and 15, 30, 60 and 90 minutes after glucose loading, and were assayed for blood glucose. The glucose tolerance of the rats was estimated by the increase in blood glucose during the 90 minutes after glucose loading, i.e., $$\sum_{0-90} \Delta BG \text{ (mg/dl)}.$$

The results obtained are shown in Table 3.

Table 3

|  | Dose (mg/kg) | $\sum_{0-90} \Delta BG$ (mg/dl) Test compound | Control | Improvement of glucose tolerance** |
|---|---|---|---|---|
| Tolubutamide(3) | 20* | 179 ± 23 | 265 ± 21 | 32.6% |
| Compound A(3) | 10 | 151 ± 43 | 265 ± 21 | 43.0 |
| Compound B(7) | 10 | 52 ± 12 | 206 ± 18 | 74.8 |
| Compound C(7) | 10 | 170 ± 15 | 206 ± 18 | 17.5 |

*Given 30 minutes prior to glucose loading.

**$[1 - \frac{\Sigma \Delta BG \text{ (test)}}{\Sigma \Delta BG \text{ (control)}}] \times 100.$ Figures in the parentheses indicate the number of rats used.

II. Insulin releasing action

A saline solution containing a test compound was injected into the femoral vein of a normal male Wistar rat weighing about 200 g under pentobarbital anesthesia (5 rats/group). Control rats received a saline injection. Blood samples were taken from the tail vein before and 10, 20, 30 and 40 minutes after injection of the test compound, and were assayed for immunoreactive insulin (IRI) by the method of C. R. Morgan et al (Diabetes, 12, 115.1963). The results are shown in Table 4.

Table 4

|  | Dose (mg/kg) | Insulin Released [ΣΔIRI (0–40)]* µunit/ml serum |  |
|---|---|---|---|
| Control | — | 50 ± 8 | 42 ± 19 |
| Tolubutamide | 50 | 189 ± 26 | 141 ± 14 |
| Compound A | 25 | — | 208 ± 21 |
| Compound B | 25 | 250 ± 13 | — |
| Compound C | 25 | 214 ± 17 | — |
| Compound Q | 25 | 198 ± 16 | — |

*Increase in serum immunoreactive insulin during 40 minutes after injection of the test compound.

III. Inhibitory action on platelet aggregation

Platelet rich plasma was prepared by centrifugation (1000 rpm, 5 min.) of fresh citrated rat blood. Fifty microliters of a solution containing a test compound at various concentrations were added to 0.4 ml of the platelet rich plasma, and the mixture was stirred for 1 minute at 1100 rpm and 30° C. Then, 50 µl of a collagen suspension was added to initiate platelet aggregation, which was measured turbidometrically according to G.V.R. Born (Nature, 194, 927, 1962). The $ID_{50}$ values represent the concentration (mM) of the compound giving a 50% inhibition of the reaction rate of controlled platelet aggregation. The results are shown in Table 5.

Table 5

| Test Compound | Inhibitory Action $ID_{50}$ (mM) |
|---|---|
| Compound A | 0.32 |
| Compound B | 0.05 |
| Compound C | 0.12 |
| Compound D | 0.27 |
| Compound E | 0.13 |
| Compound F | 0.48 |

IV. Effect on serum lactate level

An aqueous solution or suspension of a test compound was orally administered to a normal male Wister rat weighing about 200 g at a daily dose of 200 mg/kg body weight for 4 days (5 rats/group). Blood samples were taken consecutively from the tail vein, and were assayed for serum lactate by the method of Hans-Jurgens Hohorst (Methods of Enzymatic Analysis, ed. by Hans Ulrich Bergmayer, Academic Press Inc., New York, 1965). The results obtained are shown in Table 6.

Table 6

|  | Percent of Initial Serum Lactate | | Initial Serum Lactate (mole/ml) |
|---|---|---|---|
|  | 24 hrs* | 76 hrs** |  |
| Compound A | 114.9 | 94.6 | 1.075 ± 0.062 |
| Compound B | 139.6 | 113.3 | 0.993 ± 0.051 |
| Phenformin | 196.6 | 283.6 | 1.061 ± 0.099 |
| Compound Z*** (known Compound) | 152.1 | 218.8 | 1.267 ± 0.085 |

*Just before the 2nd dosing
**3 hours after the last dosing
***In this experiment, 3 rats died V. Effect of long-term administration of Compound A on streptozotocin-induced diabetic rats Diabetes was induced in male Wistar rats weighing about 170 g by a single intraperitoneal (60 mg/kg body weight) or intravenous (35 mg/kg) injection of streptozotocin. The rats showed typical symptoms of diabetes: polyphagia, polydipsia, polyuria and hyperglycemia over 400 mg glucose/dl. These rats were treated with Compound A, tolubutamide or phenformin at a daily oral dose of 25, 50 or 10 mg/kg body weight, respectively. Control diabetic rats received no treatment. The treatment was started 1 month after streptozotocin injection and continued for 4 (tolubutamide and phenformin) or 5 months (Compound A).

Fed blood glucose levels of the rats were 485 ± 18 mg/dl at the start of the treatment and 415 ± 27 (control group), 423 ± 17 (Compound A group), 447 ± 15 (tolubutamide group) and 425 ± 29 mg/dl (phenformin group) at the end of the experiment.

At the end of the experiment, the rats were sacrificed for histological examination of the kidneys and the liver and for determination of serum lipids. The results obtained are shown in Table 7.

Table 7

|  | Tolubutamide | Phenformin | Compound A |
|---|---|---|---|
| Number of rats | 8 | 7 | 7 |
| Daily dose (mg/kg) | 50 | 10 | 25 |
| Treatment month | 4 | 4 | 5 |
|  | % of control | | |
| Serum free fatty acid | 133.0 | 157.0* | 86.1 |
| Serum triglyceride | 186.8 | 225.7* | 53.0* |
| Serum cholesterol | 150.0* | 180.0* | 78.7 |

*Significant, $p < 0.05$ (vs. diabetic control)

VI. Acute Toxicity

Acute Toxicity tests were carried out in rats by oral administration. Each $LD_{50}$ was calculated from the mortality percentage on the 7th day according to the method of Litchfield and Wilcoxon. Ten male rats of the Donryu strain were used at each dose level. The results obtained are shown in Table 8.

Table 8

| Compound | $LD_{50}$(mg/kg) |
|---|---|
| Compound A | 660 |
| Compound B | 562 |
| Compound D | >1,000 |
| Compound E | >1,000 |

As can be seen from examination of the above results, the 2-substituted-1,3-diazacyclic compounds of this invention have a distinct, potent anti-diabetic activity and inhibitory action on platelet aggregation, and do not show undesirable side effects on humans and animals.

In more detail, in contrast with the increased tendency of hyperlipidemia with tolubutamide and phenformin, the compounds of this invention significantly depressed the increased tendency of serum triglyceride. Further, the present compounds do not effect the serum lactate level which may be a cause of lactic acidosis. Severe acidosis can result in hemodynamic disorders including disseminated intravascular coagulation, bradycardia and a reduction of blood pressure, ventricular contractile force and cardiac output.

Further, upon histological examination of the kidneys, the compounds of this invention did not show the diffuse glomerulosclerosis and the tublar alterations in diabetic rats, which were similar to those found in human diabetic subjects. These lesions were, to some extent, deteriorated by tolubutamide treatment.

A suitable dosage amount to be administered, e.g., orally, can range from about 2 to 15 mg/kg per about 60 kg of body weight in single or multiple doses along with an appropriate pharmaceutically acceptable carrier and diluent in the form of a tablet, a capsule or a powder, if desired. Suitable pharmaceutically acceptable carriers include lactose, sucrose, sorbitol, starch, gelatin, etc., and suitable pharmaceutically acceptable diluents include magnesium stearate, polyethylene glycol, etc.

Several specific synthesis examples of compounds within this invention are given below for purposes of illustration.

SYNTHESIS EXAMPLE 1

A mixture of 7.3g of benzhydrylamine, 4.88g of 2-methylmercapto-2-imidazoline.hydroiodide and 10 ml of methanol was refluxed for 3 hours. After cooling, methanol was distilled off and 10 percent sodium hydroxide was added to the resulting residue. The solution was extracted with 200 ml of chloroform. The chloroform solution was then washed with water and dried. After distilling off chloroform and unreacted benzhydrylamine in vacuo, a small amount of acetone was added to the resulting residue to give 3.2 g of crystals of 2-benzhydrylimino-imidazolidine having a melting point of 189°–191° C.

| | Elemental Analysis for $C_{16}H_{17}N_3$ | | |
|---|---|---|---|
| | C | H | N |
| Calcd. | 76.46 | 6.82 | 16.72 |
| Found | 76.69 | 6.88 | 16.96 |

SYNTHESIS EXAMPLE 2

A mixture of 22 g of benzhydrylamine and 5.2 g of 2-nitroamino-2-imidazoline was heated at 180° C. to 200° C. for 30 minutes. The reaction mixture was then treated in the same manner as in Synthesis Example 1 to give 0.8g of crystals of 2-benzhydryliminoimidazolidine.

SYNTHESIS EXAMPLE 3

A mixture of 2.26 g of benzhydrylamine and 30 ml of an ethyl ether solution containing 2.5 g of 2-chloro-2-imidazoline was allowed to stand at room temperature for 2 days. The reaction mixture was then treated in the same manner as in Synthesis Example 1 to give crystals of 2-benzhydryliminoimidazolidine. The crystals were dissolved in methanol and an equivalent amount of concentrated hydrochloric acid solution was added. The solution was distilled off in vacuo to give 3.2 g of 2-benzhydryliminoimidazolidine hydrochloride having a melting point of 207°–209° C.

| | Elemental Analysis for $C_{16}H_{18}N_3Cl$ | | |
|---|---|---|---|
| | C | H | N |
| Calcd. | 66.77 | 6.30 | 14.60 |
| Found | 66.81 | 6.31 | 14.63 |

SYNTHESIS EXAMPLE 4

A mixture of 1.8 g of benzhydrylamine and 3.4 g of 1-methyl-2-methylmercapto-2-imidazoline.hydroiodide was allowed to stand at room temperature for 2 days. Chloroform was then distilled off to give 1.2 g of 1-methyl-2-benzhydryliminoimidazolidine.hydroiodide having a melting point of 254°–256° C.

| | Elemental Analysis for $C_{17}H_{20}N_3I$ | | |
|---|---|---|---|
| | C | H | N |
| Calcd. | 67.65 | 6.68 | 13.92 |
| Found | 67.91 | 6.84 | 13.94 |

SYNTHESIS EXAMPLE 5

A mixture of 3.37 g of α-(p-chlorophenyl)benzylamine and 4.54 g of 2-methylmercapto-2-imidazoline-hydroiodide was heated at 150°–160° C. for 20 minutes. After cooling, the reaction mixture was dissolved in methanol and the solution rendered basic with sodium hydroxide to give 2-(α-(p-chlorophenyl)benzyl)iminoimidazolidine having a melting point of 187°–189° C.

SYNTHESIS EXAMPLES 6-9

By repeating substantially the same procedure as in Example 5, except for varying the starting materials, the following derivatives shown in Table 9 were prepared.

SYNTHESIS EXAMPLE 12

A mixture of 5.46 g of N-benzyhydryl-S-methylisothiuroniumiodide, 8.53 g of ethylenediamine and 40 ml of methanol was refluxed for 15 hours. After cooling, methanol and unreacted ethylenediamine were distilled Table 9

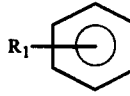

off in vacuo. The resulting residue was dissolved in 30 ml of ethanol, reudered basic with sodium hydroxide and extracted with chloroform. The chloroform solution was washed with water, dried and evaporated to give a crystalline residue which was recrystallized from isopropyl alcohol to give 2.7 g of pure 2-benzhydryliminoimidazolidine having a melting point of 189°–190° C.

SYNTHESIS EXAMPLE 10

3.6 g of sodium hydride was dissolved in 20 ml of water and the solution was cooled in an ice bath. To the solution, there was added 6.0 g of 2-chloroimidazolidine.sulfate. The solution was extracted with chloroform three times and the chloroform layer then dried. To the chloroform solution was then added 3.0 g of methylbenzhydrylamine and the solution allowed to stand 2 days. The solution was then evaporated. The residue was dissolved in 50 ml of water and washed with ethyl ether. The aqueous solution was rendered basic with sodium hydroxide. The resulting crystals were collected by filtration, washed with water and dried to give 4.0 g of 2-(N-methyl, N-benzhydryl)-amino-2-imidazoline having a melting point of 161°–162° C.

SYNTHESIS EXAMPLE 13

A mixture of 3.84 of N-benzydryl-s-methylisothiuroniumiodide and 7.5 g of 1,3-propanediamine and 25 ml of methanol was refluxed for 16 hours.

The reaction mixture was then subjected to substantially the same treatment as in Example 6 to give crude 2-benzhydrylimino-1,3-diazacyclohexane.

The crude compound was added to methanol containing hydrochloric acid to give 3.3 g of 2-benzhydrylimino-1,3-diazacyclohexane having a melting point of 238°–242° C.

| | Elemental Analysis for $C_{17}H_{19}N_3$ | | |
|---|---|---|---|
| | C | H | N |
| Calcd. | 76.94 | 7.22 | 15.92 |
| Found | 76.96 | 7.23 | 15.89 |

| | Elemental Analysis for $C_{17}H_{20}N_3Cl$ | | |
|---|---|---|---|
| | C | H | N |
| Calcd. | 67.65 | 6.68 | 13.92 |
| Found | 66.77 | 6.67 | 13.70 |

SYNTHESIS EXAMPLE 11

By repeating substantially the same procedure as in Example 10 except for varying the starting materials, 2-(N-ethyl, N-benzhydryl)amino-2-imidazoline having a melting point of 141°–142° C. was prepared.

SYNTHESIS EXAMPLES 14-25

By repeating substantially the same procedure as in Example 13 except for varying the starting materials, various other 1,3-diazacycloalkane derivatives were prepared. The results obtained are summarized in the following Table 10.

Table 10

[Structure: R1-phenyl-CHR6-N=C(NR2)(NR3) with (CH2)n bridge to R4]

| Example No. | R1-phenyl-R6 | R2 | R3 | (CH2)n with R4 | Melting Point (°C) |
|---|---|---|---|---|---|
| 13 | phenyl, phenyl (R6) | —H | —H | —CH2—CH2—CH2— | 238 – 242° C (HCl salt) |
| 14 | " | " | " | —CH2—CH2 / —CH2—CH2 | 227 – 229.5° C (HCl salt) |
| 15 | " | " | —CH3 | —CH2—CH2— | 254 – 256° C (HCl salt) |
| 16 | " | " | —CH(CH3)2 | " | 200 – 202° C (HCl salt) |
| 17 | " | " | -n-C4H9 | " | 240 – 242° C (HCl salt) |
| 18 | " | " | " | —CH2—(phenyl)—; —CH2—CH2— | 237 – 239 (HCl salt) |
| 19 | " | " | —CH3 | —CH2—CH2—CH2— | 219 – 221 (HCl salt) |
| 20 | " | " | —H | —CH(CH3)—CH2— | 225 – 227 (HCl salt) |
| 21 | " | " | " | —CH(phenyl)—CH2— | 155 – 157 (HCl salt) |
| 22 | " | " | —CH2CH2OH | —CH2—CH2— | 132 – 135 |
| 23 | 2-Cl-phenyl, phenyl | " | —H | " | 205 – 207 (HCl salt) |

SYNTHESIS EXAMPLE 26

A mixture of 2.07 g of 2,2-diphenyl propionitrile and 2.78 g of ethylenediamine.tosylate was heated at 200° C. for 3 hours. After cooling, the solution was rendered basic with an alkali hydroxide and extracted with chloroform. The chloroform layer was washed with water and dried. After evaporating chloroform, the resulting residue was recrystallized from a mixture of benzene and hexane to give 1.4 g of 2-(2,2-diphenyl ethyl)-2-imidazoline having a melting point of 98° to 101° C. The hydrochloride thereof had a melting point of 173°–175° C.

| Elemental Analysis for $C_{17}H_{18}N_2 \cdot HCl$ | | | |
|---|---|---|---|
| | C | H | N |
| Calcd. | 71.20 | 6.68 | 9.77 |
| Found | 70.84 | 6.72 | 9.98 |

SYNTHESIS EXAMPLES 27–29

By repeating substantially same procedure as in Example 26 except for varying the starting materials, the following compounds were obtained.

SYNTHESIS EXAMPLE 27

1-methyl-2-(2,2-diphenyl ethyl)-2-imidazoline.sulfate. mp 108°–110° C.

| Elemental Analysis for $C_{18}H_{20}N_2 \cdot H_2SO_4$ | | | |
|---|---|---|---|
| | C | H | N |
| Calcd. | 59.65 | 6.12 | 7.73 |

-continued

Elemental Analysis for $C_{18}H_{20}N_2 \cdot H_2SO_4$

|  | C | H | N |
|---|---|---|---|
| Found | 59.58 | 6.08 | 7.64 |

SYNTHESIS EXAMPLE 28

2-(2,2-diphenyl)ethyl-1,4,5,6-tetrahydropyrimidine.-hydrochloride. mp 173°–175° C.

SYNTHESIS EXAMPLE 29

2-(2,2-diphenyl ethyl)-1,5,6,7-tetrahydro-1,3-diazepine. hydrochloride. mp 190°–192° C.

SYNTHESIS EXAMPLE 30

A mixture of 6.9 of 2-phenyl-2-cyclohexyl propionitrile and 8.0 of ethylenediamine-tosylate was heated at about 200° to 210° C. for 3 hours. The reaction mixture was then treated in the same manner as in Example 26 to give 5.7 g of 2-(2-phenyl-2-cyclohexyl ethyl)-2-imidazolidine having a melting point of 75° to 77° C.

SYNTHESIS EXAMPLE 31

A mixture of 2.6 of ethyl 2-phenyl-2-(4-pyridyl)propionate and 10 g of ethylenediamine was refluxed for 10 hours. After removing unreacted ethylenediamine by distillation, the resulting residue was heated at 210° to 230° C. for 3 hours. The reaction mixture was then treated in the same manner as in Example 26 to give 2-[2-phenyl-2-(4-pyridyl)ethyl]-2-imidazoline having a melting point of 105°–107° C.

SYNTHESIS EXAMPLE 32

A mixture of 5.06 of ethyl 2,2-diphenylpropioiminoether and 1.8 of 1,2-propanediamine was heated at 140°–150° C., for one hour. After cooling, the reaction mixture was subjected to alumina column chromatography and eluted with a mixture of benzene and ethyl acetate. The solvent was removed by distillation from the eluate to give 4.2 g of 2-(2,2-diphenylethyl)-4-methyl-2-imidazoline having a melting point of 55°–57° C.

SYNTHESIS EXAMPLE 33

A mixture of 1.25 g of 2-benzhydryliminoimidazoline, 0.16 g of sodium hydride and 7 ml of dried dimethylformamide was stirred at room temperature for 20 minutes. Then, 1.0 g of methyl iodide was added to this solution and the solution was stirred for a further two hours. After the reaction, dimethylformamide was evaporatted off in vacuo and a small quantity of water was added and the system then extracted with chloroform. The chloroform layer was washed with water and dried. After evaporating chloroform, the resulting residue was dissolved in a small quantity of methanol and to this solution was added hydrochloric acid. Methanol was evaporated from the solution to give 0.95 g of 1-methyl-2-benzhydrylimino imidazoline hydrochloride having a melting point of 254°–256° C.

SYNTHESIS EXAMPLES 34–38

By repeating substantially the same procedure as in Example 33 except for varying the starting materials, various other 1,3-diazacycloalkane derivatives were prepared. The results obtained are summarized in the following Table 11.

Table 11

| Example No. | $R_1$—phenyl / $R_6$ | $R_6$ | $R_2$ | $R_3$ | $(CH_2)_n$ / $R_4$ | Melting Point (° C) |
|---|---|---|---|---|---|---|
| 34 | phenyl | phenyl | —H | —C$_2$H$_5$ | —CH$_2$—CH$_2$ | 274 – 276 (HCl salt) |
| 35 | " | " | " | " | —CH$_2$—CH$_2$—CH$_2$ | 247 – 249 (HCl salt) |
| 36 | 4-Cl-phenyl | " | " | —CH$_3$ | —CH$_2$—CH$_2$ | 206 – 208 (H$_2$SO$_4$ salt) |
| 37 | phenyl | 2-pyridyl | " | " | " | 127 – 129 |

Table 11-continued

[Structure diagram showing benzhydryl-imidazolidine compound with substituents R1, R2, R3, R4, R6 and (CH2)n]

| Example No. | R1, R6 | R2, R3 | (CH2)n / R4 | Melting Point (°C) |
|---|---|---|---|---|
| 38 | " | " " | " | 221 – 223 (HCl salt) |
|    | (cyclohexyl, H) | | | |

SYNTHESIS EXAMPLE 39

To a mixture of 2.51 g of 2-benzhydryliminoimidazolidine and 50 ml of dimethylformamide was added 0.6 g of sodium hydride. After stirring for 10 minutes, 2.55 g of acetic anhydride was added to the solution. The solution was stirred at room temperature for a further 3 hours and solvent then evaporated. To the residue was added 100 ml of water and the system extracted with chloroform. The resulting chloroform layer was washed with water and dried with sodium sulfate. After evaporating chloroform, the resulting residue was dissolved in methanol. Hydrochloric acid was then added to the solution to give 1-acetyl-2-benzhydryliminoimidazolidine. hydrochloride having a melting point of 234° to 236° C.

| | Elemental Analysis for $C_{17}H_{19}N_3O \cdot HCl$ | | |
|---|---|---|---|
| | C | H | N |
| Calcd. | 65.55 | 6.11 | 12.74 |
| Found | 65.55 | 6.31 | 12.64 |

SYNTHESIS EXAMPLE 40

A mixture of 0.50 g of 2-benzhydrylimino-1,3-diazacycloheptane and 0.237 g of acetic anhydride was reacted in substantially the same procedure as in Example 40 to give 1-acetyl-2-benzhydrylimino-1,3-diazacycloheptane having a melting point of 250° to 252° C.

| | Elemental Analysis for $C_{20}H_{23}N_3O$ | | |
|---|---|---|---|
| | C | H | N |
| Calcd. | 74.73 | 7.21 | 13.07 |
| Found | 74.59 | 7.02 | 13.25 |

SYNTHESIS EXAMPLE 41

To a mixture of 1.0 g of 1-methyl-2-benzhydryliminoimidazolidine, 10 ml of chloroform and 0.42 g of triethylamine was added a mixture of 0.33 g of acetyl chloride and 5 ml of chloroform while cooling. The mixture was further reacted at room temperature for about 2 hours, washed with water and dried with sodium sulfate. Chloroform was evaporated from the solution to give 1-acetyl-2-benzhydryl-3-methylimidazolidine having a melting point of 164° to 165° C.

| | Elemental Analysis for $C_{19}H_{21}N_3O$ | | |
|---|---|---|---|
| | C | H | N |
| Calcd. | 74.24 | 6.89 | 13.67 |
| Found | 74.54 | 6.93 | 13.58 |

SYNTHESIS EXAMPLES 42–51

By repeating substantially the same procedure as in Example 41 except for varying the starting materials, various other 1,3-diazacyclic compounds were prepared. The results obtained are summarized in the following Table 12.

Table 12

General structure:

R1—(phenyl)—C(R6)=N—N(R2)(...)—N(R3)—(CH2)n with R4 branch

| Example No. | R1-phenyl | R6 | R2 | R3 | R4/(CH2)n | Melting Point (°C) |
|---|---|---|---|---|---|---|
| 42 | phenyl | phenyl | —CH3 | —COC3H7 | —CH2—CH2 | 100 – 101 |
| 43 | " | " | " | —COOC2H5 | " | 94 – 95 |
| 44 | " | " | " | —CO—(furyl, O) | " | 154 – 155 |
| 45 | " | " | " | —CO—(thienyl, S) | " | 139 – 140 |
| 46 | " | " | " | —CO—(pyrrolyl, N) | " | 168 – 170 |
| 47 | " | " | " | —CO—phenyl | " | 157 – 158 |
| 48 | " | " | " | —CO—(2-Cl-phenyl) | " | 176 – 177 |
| 49 | " | " | " | —CO—(4-Cl, 2-CH3O-phenyl) | " | 197 – 198 |
| 50 | " | " | " | —CO—(4-OCOCH3-phenyl) | " | 141 – 143 |
| 51 | " | " | " | —CO—(4-COCH3-phenyl) | " | 124 – 125 |

SYNTHESIS EXAMPLE 52

A mixture of 2.5 g of 2-(2,2-diphenyl ethyl)-2-imidazoline and 50 ml of ethylformate was refluxed for 5 hours. After the reaction, unreacted ethylformate was removed by distillation. The resulting residue was subjected to silica gel column chromatography and eluted with methylene chloride. The solvent was removed by distillation from the eluate to give 1.2 g of 1-formyl-2-(2,2-diphenyl ethyl)-2-imidazoline having a melting point of 105° to 107° C.

SYNTHESIS EXAMPLE 53

To a mixture of 5.0 g of 2-(2,2-diphenyl ethyl)-2-imidazoline and 50 ml of pyridine, 1.1 g of acetyl chloride was dropwise added and the solution stirred at room temperature for about 2 hours. After the reaction, pyridine was removed by distillation. To the resulting residue there was added 100 ml of benzene and the same amount of water, and the solution was well shaken. The benzene layer was separated, washed with water and dried with sodium sulfate. After removing benzene from the solution, the resulting residue was recrystallized from ether to give 1-acetyl-2-(2,2-diphenyl ethyl)-2-imidazoline having a melting point of 104°-106° C.

SYNTHESIS EXAMPLE 54

In place of acetyl chloride in Example 53, ethyl chlorocarbonate was reacted with 2-(2,2-diphenyl ethyl)-2-imidazoline to give 1-ethoxycarbonyl-2-(2,2-diphenyl ethyl)-2-imidazoline having a melting point of 78° to 80° C.

SYNTHESIS EXAMPLE 55

A mixture of 0.75 g of 2-(2,2-diphenyl ethyl)-2-imidazoline, 0.3 g of paraformaldehyde and 5 ml of benzene was refluxed about 2 hours to give 1-hydroxymethyl-2-(2,2-diphenyl ethyl)-2-imidazoline having a melting point of 161° to 163° C.

SYNTHESIS EXAMPLE 56

To a mixture of 1.0 g of 2-(N-methyl, N-benzhydryl)amino-2-imidazoline, 10 ml of chloroform and 0.42 g of triethylamine, was added 0.33 g of acetyl chloride while cooling and the solution was stirred at room temperature for one hour. The solution was then washed with water and dried with sodium sulfate, whereafter chloroform was distilled off to give 0.8 g of 1-acetyl-2-(N-methyl, N-benzhydryl)amino-2-imidazoline having a melting point of 99 to 101° C.

While the invention has been described in detail and with reference to specific embodiments thereof, it will be apparent to one skilled in the art that various changes and modifications can be made therein without departing from the spirit and scope thereof.

What is claimed is:

1. A method of treating diabetes mellitus comprising administering a therapeutically effective amount for treating diabetes mellitus of at least one compound of the following structural formula or pharmaceutically acceptable salt thereof to a patient in need of such treatment:

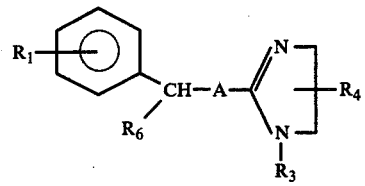

wherein $R_1$ represents a hydrogen atom, a halogen atom, a lower alkyl group, or a lower alkoxy group; $R_3$ represents a hydrogen atom, a lower alkyl group, or a lower hydroxyalkyl group; $R_4$ represents a hydrogen atom or a lower alkyl group; $R_6$ represents a phenyl group which may have a substituent selected from a halogen atom, a lower alkyl group and a lower alkoxy group; and A represents a -$CH_2$- group.

2. The method of claim 1 wherein said compound is 2-(2,2-diphenyl)ethyl imidazoline.

3. The method of claim 1 wherein said compound is 1-methyl-2-(2,2-diphenyl ethyl) imidazoline.

* * * * *